United States Patent

Mattson et al.

Patent Number: 6,092,928
Date of Patent: Jul. 25, 2000

[54] APPARATUS AND METHOD TO DETERMINE THE RELATIVE POSITION OF A DETECTOR ARRAY AND AN X-RAY TUBE FOCAL SPOT

[75] Inventors: Rodney A. Mattson, Mentor; Pieter G. Roos, Bainbridge, both of Ohio

[73] Assignee: Picker International, Inc., Highland Heights, Ohio

[21] Appl. No.: 09/191,094

[22] Filed: Nov. 12, 1998

[51] Int. Cl.⁷ ..................................................... A61B 6/08
[52] U.S. Cl. ......................... 378/205; 378/98.2; 378/197; 378/207
[58] Field of Search ................... 378/98.2, 197, 378/205, 207

[56] References Cited

U.S. PATENT DOCUMENTS

| | | | |
|---|---|---|---|
| 4,803,712 | 2/1989 | Kembo et al. | 378/34 |
| 4,935,948 | 6/1990 | Kim | 378/125 |
| 5,159,623 | 10/1992 | Niepel | 378/197 |
| 5,170,439 | 12/1992 | Zeng et al. | 382/6 |
| 5,291,540 | 3/1994 | Futamata | 378/197 |
| 5,553,113 | 9/1996 | Weedon | 378/98.5 |
| 5,592,523 | 1/1997 | Tuy et al. | 378/19 |
| 5,625,660 | 4/1997 | Tuy . | |
| 5,757,951 | 5/1998 | Tuy | 382/131 |
| 6,031,891 | 2/2000 | Roos et al. | 378/98.2 |

OTHER PUBLICATIONS

U.S. application No. 09/164,013, Tuy, filed Sep. 30, 1998.
Analog Devices, Inc. Accelerometer Product, Oct. 1998 http://www.analogdevices.com/industry/items.
Summit Instruments, Inc. Accelerometer Product, Oct. 1998 http://www.summitinstruments/com/accel/index.htm.
Analog Devices, Inc. Accelerometer News Oct. 1998 http://www.analogdevices.com/publications/magazines/accel news/issue6/4.htm.
"Dynamic Geometrical Calibraton for 3–D Cerebral Angiography", N. Nauab et al., SPIE vol. 2708/361 (1996).
"Characterization of a C–arm Mounted XRII for 3D Image Reconstruction During Interventional Neuroradiology", R. Fahrig, et al., SPIE vol. 2708/351 (1996).
"Three–Dimensional Computed Tomographic Reconstruction Using a C–arm Mounted XRII: Correction of Image Intensifier Distortion", R. Fahrig, et al., Med. Phys., 24(7), 1097 (1997).
"Use of a C–arm System to Generate True Three–Dimensional Computed Rotational Angiograms: Preliminary In Vitro and In Vivo Results", R. Fahrig et all., Am. J. Neuroradiol 18:1507 (1997).

Primary Examiner—David V. Bruce
Assistant Examiner—Allen C. Ho
Attorney, Agent, or Firm—Fay, Sharpe, Fagan, Minnich & McKee, LLP

[57] ABSTRACT

An x-ray source (30) transmits a beam of x-rays through an examination region (E). A detector (28), in an initial spatial orientation relative to the source, receives the beam and generates a view of image data indicative of the intensity of the beam received. A first accelerometer (40), capable of generating acceleration data in at least one dimension, is associated with the detector. A second accelerometer (42), capable of generating acceleration data in at least one dimension is associated with the source. A position calculator (60) mathematically calculates a position of both the source and detector based on the acceleration data generated by the accelerometers. An image reconstructor (62) receives the relative position data; electronically corrects for any misalignment or change in beam travel distance, and reconstructs the views into a volumetric image representation.

21 Claims, 5 Drawing Sheets

APPARATUS AND METHOD TO DETERMINE THE RELATIVE POSITION OF A DETECTOR ARRAY AND AN X-RAY TUBE FOCAL SPOT

BACKGROUND OF THE INVENTION

The present invention relates to the art of medical imaging. It finds particular application in conjunction with C-arm supports for generating three-dimensional computed tomography imaging data, more particularly fluoroscopic x-ray systems, and will be described with particular reference thereto. It is to be appreciated, however, that the invention is also applicable to other real-time imaging systems capable of monitoring a region of a patient during a minimally invasive procedure.

In some operating rooms, such as operating rooms for vascular catheter procedures, a projection x-ray imaging device is provided in association with the operating table. More specifically, an x-ray tube or generator and an x-ray detector are mounted on a C-arm which is positioned such that the area of interest or patient lies between the x-ray source and detector. The x-ray source and detector are rotatable and longitudinally displaceable as a unit to select a region and angle for projection imaging. Once the surgeon has positioned the x-ray source and detector in the proper position, the surgeon actuates the x-ray tube sending x-rays through the patient and onto the x-ray detector for a preselected exposure time. The x-rays received by the detector are converted into electronic, video image data representing a projection or shadow-graphic image. The projection or shadow-graphic image is displayed on a video monitor which is viewable by the physician.

In cardiac catheterization procedures, for example, images are generated to show the vasculature system and monitor the advance of the catheter through the blood vessels. More specifically, the surgeon advances the catheter into the patient, stops the surgical procedure, and initiates an x-ray imaging procedure. The x-rays are converted into electronic data and a projection image is displayed.

One of the drawbacks of these x-ray systems is that the resultant image is a projection or shadow-graphic image. That is, the 3-D vasculature system of the patient is projected into a single plane.

If 3-D diagnostic images are required, such images are often taken with a CT scanner or a magnetic resonance imaging device which is typically located in another part of the facility. Thus, any three-dimensional diagnostic images are commonly generated sometime before the surgical procedure starts. Even if a CT scanner is present in the surgical suite, the patient is still moved into the scanner. The transportation of the patient to the CT or MRI machine for further imaging often renders three-dimensional images impractical during surgery.

However, three-dimensional images obtained are valuable during surgical procedures. After generating a three-dimensional diagnostic image, a surgical procedure is commenced, such as a biopsy. From time to time during the procedure, additional projection diagnostic images are generated to monitor the advancement of the biopsy needle into the patient. The location of the needle can be mathematically predicted from the projection images and monitoring of the physical position of the needle or other instrument can be superimposed on the 3-D diagnostic images. As the needle moves, the superimposed images can be altered electronically to display the needle in the proper position. Various trajectory planning packages have been proposed which would enable the operator to plan the biopsy procedure in advance and electronically try various surgical paths through the three-dimensional electronic data.

Recently, there has been some interest in using relatively low power fluoroscopic systems to generate real time three-dimensional CT reconstructions. Such a technique, disclosed in U.S. Ser. No. 08/802,618 to Barni, is assigned to the assignee of this invention. Barni suggests operating the x-ray tube of a CT scanner in a fluoroscopic mode. Unfortunately, the complete, encircling CT gantry can obstruct access to the surgical site or make that access inconvenient or uncomfortable for the physician.

Another solution disclosed by R. Fahrig, et al. in SPIE Volume 2708 entitled "Characterization Of A C-Arm Mounted XRII For 3-D Image Reconstruction During Interventional Neuro Radiology" recognizes that a C-arm would provide improved access to the surgical site. The Fahrig article also observes that the C-arm lacks sufficient rigidity to prevent the x-ray source and the detector plates from moving relative to each other, especially during a volume scan where the source and the detector are rotated about an area of interest. Relative motion misaligns the apparatus and causes image degradations. The Fahrig article describes a method wherein the motions and the deflections of the C-arm are premeasured or estimated in pilot scans. The deflections are assumed to remain the same for subsequent scans performed from the same starting point and within all other parameters. System calibration is performed by inserting a three-dimensional phantom containing metal beads or the like with known locations into the imaging field and performing a representative scan. Subsequent image analysis is used to determine positional errors, due to C-arm distortion and deflection. By comparing the detected position of the beads in each image with calculated ideal positions that would occur in the absence of any C-arm distortion errors are calculated. These errors, for each image scan, are stored in a long-term memory and applied to all subsequent scans, correcting for the calibration errors. Unfortunately, the Fahrig method requires that all volume imaging scans begin in exactly the same location and travel through the same arc. Moreover, any changes in the mechanical characteristics of the C-arm, such as bearing wear, changes in the source to image distance, drive speed, etc., will cause a deterioration in image quality due to the application of improper positional corrections.

The present invention provides a new and improved method and apparatus which overcomes the above-referenced problems and others.

SUMMARY OF THE INVENTION

In accordance with the present invention, a diagnostic imaging apparatus includes an x-ray source for transmitting a beam of x-rays through an examination region. An accelerometer is associated with the x-ray source such that a change in linear velocity of the source corresponds to an acceleration reading being registered by the accelerometer.

In accordance with a more limited aspect of the present invention, the diagnostic imaging apparatus includes a second accelerometer for measuring acceleration of the detector.

In accordance with a more limited aspect of the present invention, a position calculator mathematically calculates a position of both the source and the detector from data including signals provided by the accelerometers.

In accordance with a more limited aspect of the present invention, an image reconstruction processor is included to receive a plurality of image data views and for processing the views into a three-dimensional image representation using the calculated position data.

In accordance with a more limited aspect of the present invention, the diagnostic imaging apparatus also includes a collimator movably mounted to the x-ray source for restricting the cone beam of x-rays onto the detector. A misalignment processor receives the position data and controls a drive system mechanically linked to the collimator.

One advantage of the present invention resides in the acquisition and display of more accurate volumetric images.

Another advantage of the present invention resides in computationally simpler and more efficient image signal manipulation.

Another advantage of the present invention resides in the ability to obtain volume scans from any starting and stopping position.

Another advantage of the present invention resides in the ability to provide dynamic corrections without relying on periodic calibration with three-dimensional phantoms.

Yet other benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
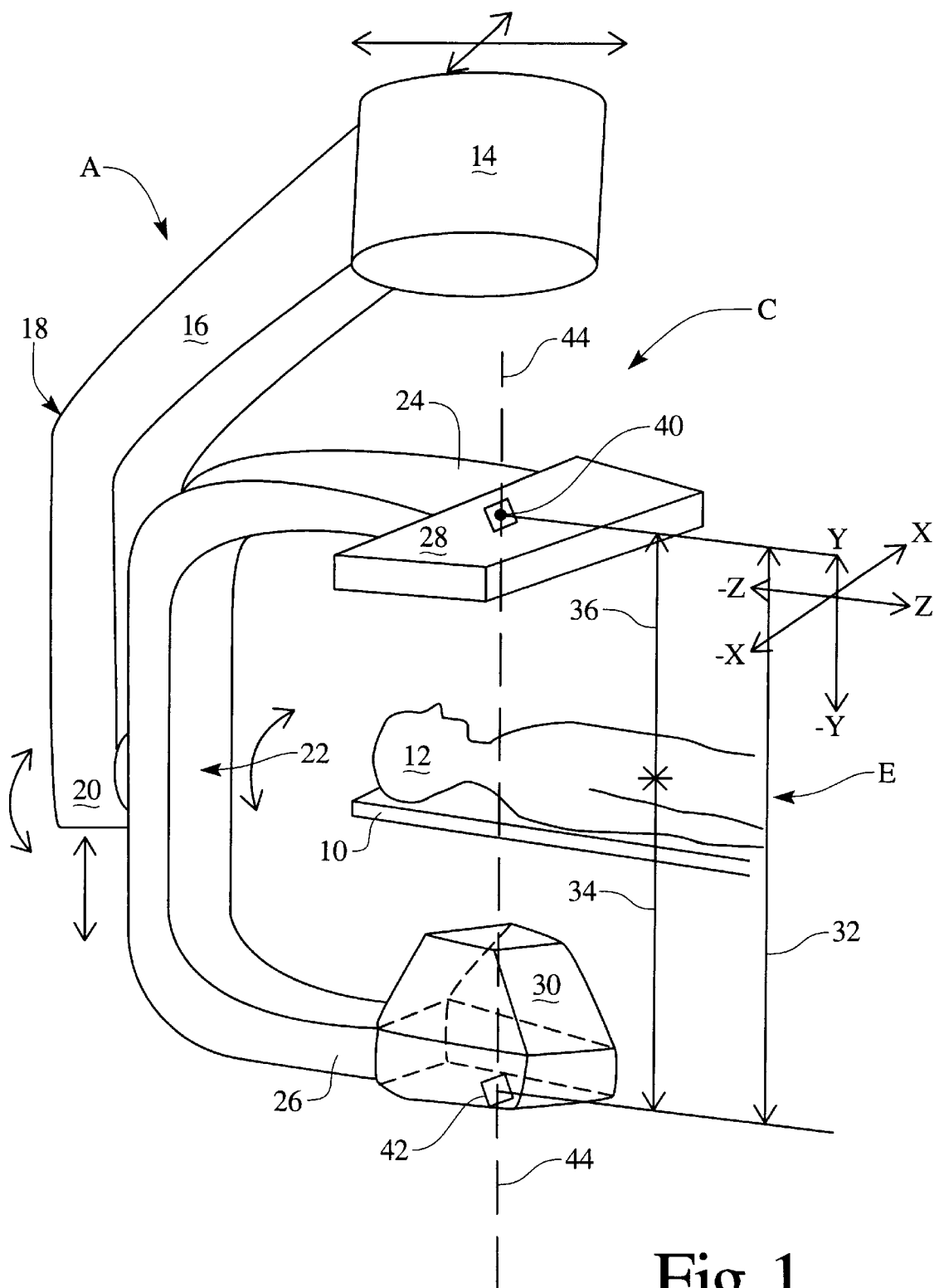
FIG. 1 is a diagrammatic illustration of an imaging system in accordance with the present invention.

With reference to FIG. 1, a C-arm C is supported by a rotational support assembly A, for rotation around an examination region E. The examination region E is describable by orthogonal axes X, Y, and Z. An x-ray transparent couch 10 is positioned such that a region of interest of a subject 12 is positioned in the examination region E. Vertical and horizontal drives (not shown) move the couch to facilitate positioning the region of interest at the center or other appropriate location in the examination region E. Alternatively, the rotational support assembly arm A moves in the X or Z direction.

The rotational support assembly A includes an overhead rotational mount or bearing 14 mounted to a ceiling or other overhead fixture for rotation about a vertical axis Y. In one preferred embodiment, the overhead rotational mount 14 is movably fixed to a track or other mechanism also allowing movement in the X and Z directions. An arm 16 extends away from the overhead mount 14 in the -Y direction through an elbow 18 to a lower rotational mount or bearing 20 with a horizontal axis of rotation.

A midpoint 22 of the C-arm C is rotatably attached to the lower bearing 20. The C-arm C defines two opposing parallel ends 24, 26, on either side of the examination region E. A detector 28, such as a flat panel detector or the like for detecting x-ray radiation, is attached to the first end 24. The detector 28 is preferably a solid state device, such as a grid of amorphous silicon detector elements, that generate x-ray intensity signals for each element of the grid. An x-ray source 30 is attached on the second end 26 of the C-arm. The C-arm C has sufficient strength to maintain the detector 28 and x-ray source 30 with a substantially fixed spatial relationship. However, due to the mass of the x-ray tube and the arms, the ends 24, 26 deflect or move during positioning. On stopping the ends oscillate, but dampen back to the fixed position.

In order to obtain three-dimensional images, the source 30 and the detector 28 are rotated in a plane perpendicular to the axis of the lower bearing 20 i.e. in the X-Y plane. Elongated volume scans can also be achieved by adding relative motion along the Z axis. Accurate three-dimensional reconstruction requires an accurate knowledge of the x-ray path through the examination region E and a distance 32 between the detector 28 and the source 30, more particularly a distance 34 between the source 30 and the region of interest and a distance 36 between the region of interest and the detector 28.

In a preferred embodiment, the detector 28 and the x-ray source 30 both include three-dimensional Micro-Electro-Mechanical (MEMS) accelerometers 40, 42. MEMS accelerometers are known and commercially manufactured. The accelerometers 40, 42 are positioned ideally along a central axis 44 passing through a geometric center of the detector 28 and a center of a focal spot on the source 30 for mathematical convenience. However, it is appreciated that the accelerometers could also be located at other known positions within the housings of the detector and the source offset from the central axis. Moreover, in addition to MEMS devices, use of other accelerometers or accurate position sensing devices is also envisioned by the present invention such as gyroscopes, inertial sensors, and the like.

Figure 2:
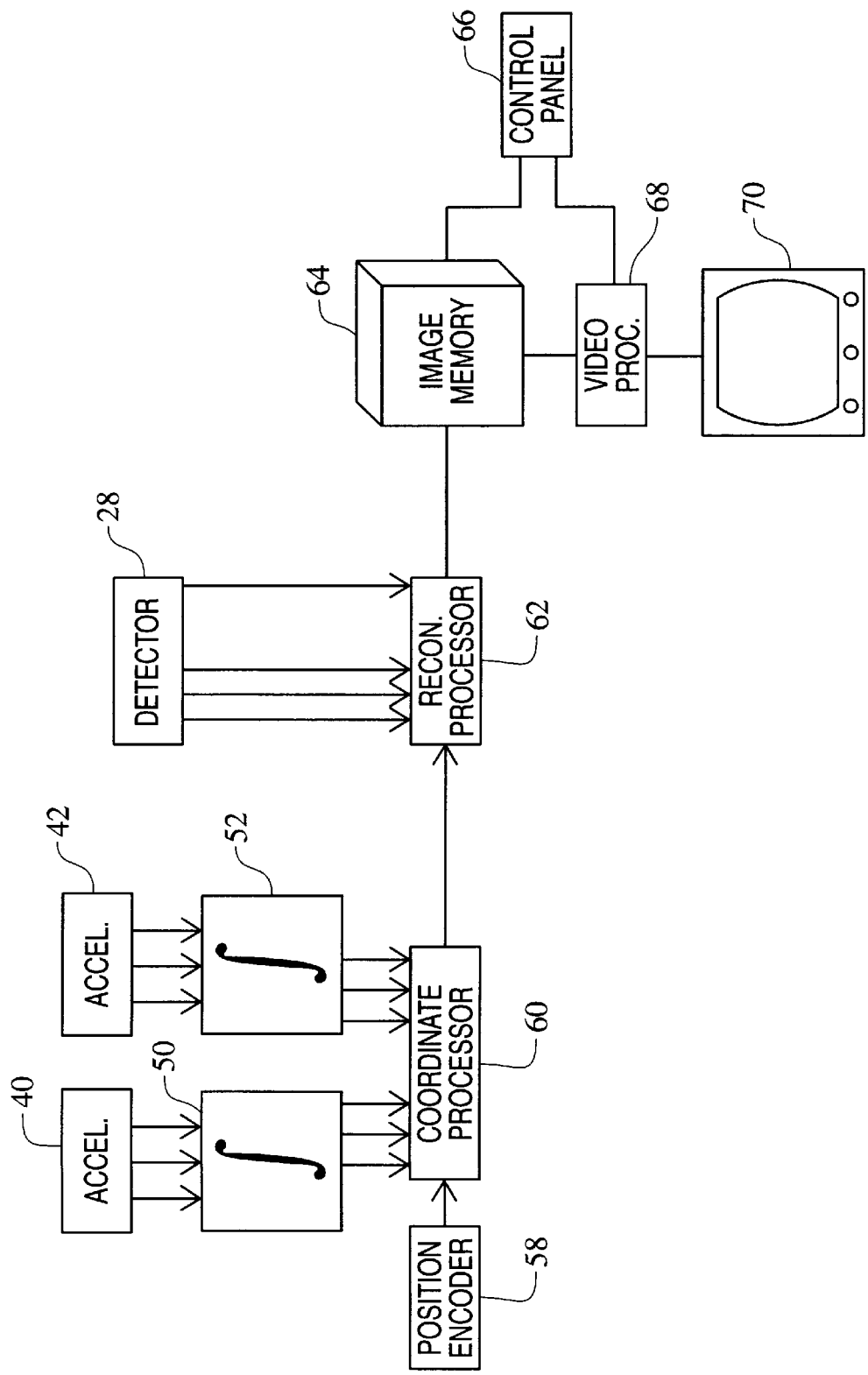
FIG. 2 is a block diagram of a signal processor in accordance with the present invention.

Now referring to FIG. 2, the accelerometers 40, 42 each generate electronic acceleration data indicative of acceleration along volumetric coordinates. Integrators 50, 52 perform a double integral on the acceleration data along each of the coordinates to determine cumulative displacement relative to each coordinate from an initial starting point. At each data sampling point, the integrators 50, 52 are sampled to provide the deflection error corresponding to each view of image data. It is to be appreciated that, the accelerometers and integrators can provide the displacement data in rectangular coordinates, polar coordinates, or the like. Further, depending on the motion direction and the construction of the C-arm, one can choose to determine the displacement along only one or two coordinates.

A position encoder 58 determines the initial starting position preferably in the same coordinates. A coordinate processor 60 calculates the orientation of the central axis 44, the source and detector positions for each sampling position from the starting position and the cumulative displacements. If the integrators are zeroed at the starting position, actual position can be calculated by simply adding the cumulative displacement to the starting position. Optionally, the coordinate processor 60 uses the output of the encoder 58 to determine an offset error, skew error or the like at each view sampling position. Either way, the output indicates the actual trajectory of each ray of each view through the examination region.

Figure 3:
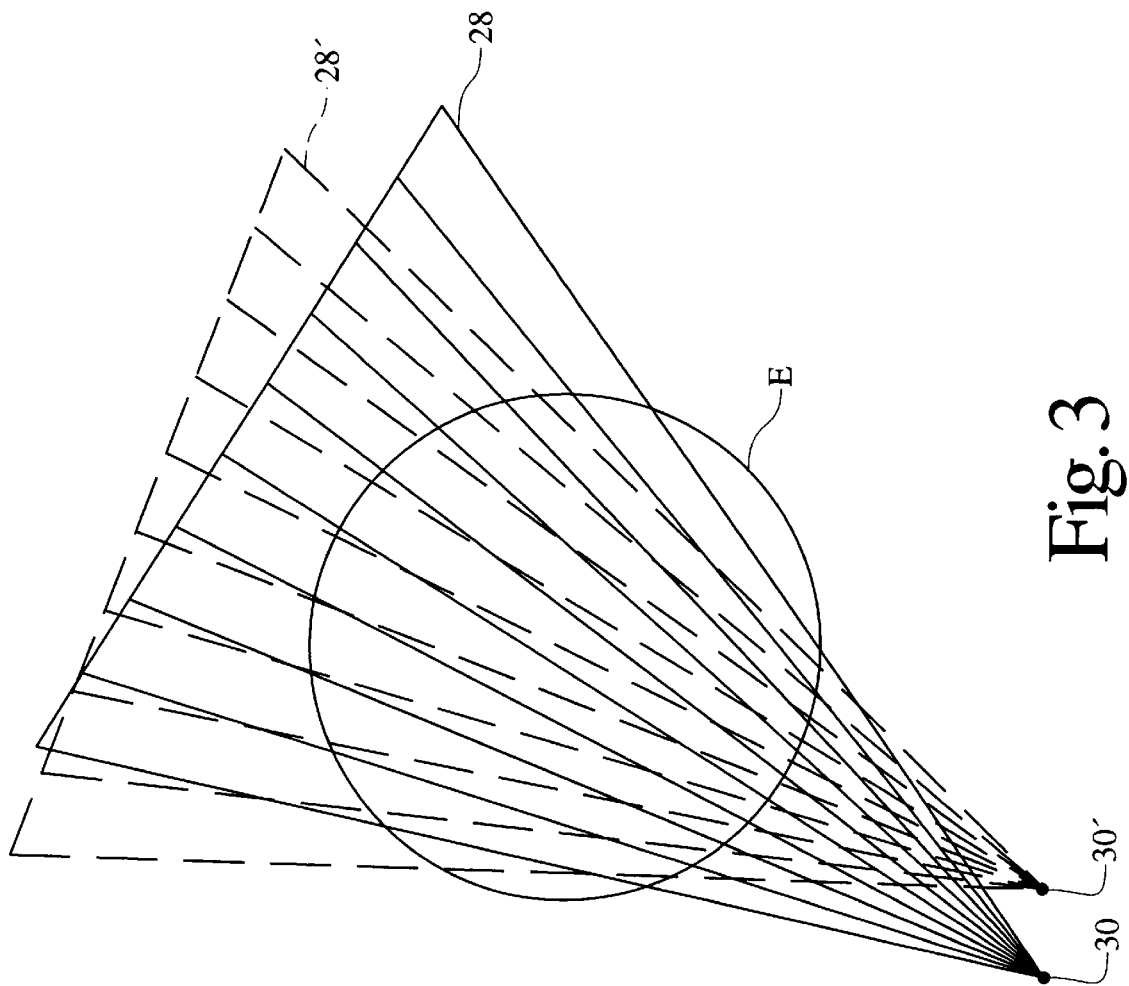
FIG. 3 is a depiction of error induced by deflection.

An image reconstruction processor 62 applies known reconstruction algorithms for cone beam data to each sampled view. Each view is convolved or otherwise processed and then back projected into a volume image memory 64. Conventional reconstruction algorithms assume that each view is collected at the selected sampling position and represents radiation attenuation along rays (shown in solid) between the source 30 and the detector 28 as shown in FIG. 3. Rather than projecting the data along the expected rays, the reconstruction processor 62 uses the actual position of the source 30' and the detector 28' to project the data along the actual rays (shown in phantom). Depending on the exact algorithm chosen, the ray trajectories are corrected by rotational offsets, angular offsets, magnification correction, redefining the ray trajectories, and the like.

The volume image is reconstructed, built, and stored as voxels in the volume memory 64. An operator control panel 66 enables the operator to select various image representations, such as slice images, slab images, volume images, and the like to be displayed. A video processor 68 samples the appropriate voxels in the volume memory and converts the data to approximate form for display on a monitor 70.

Figure 4:
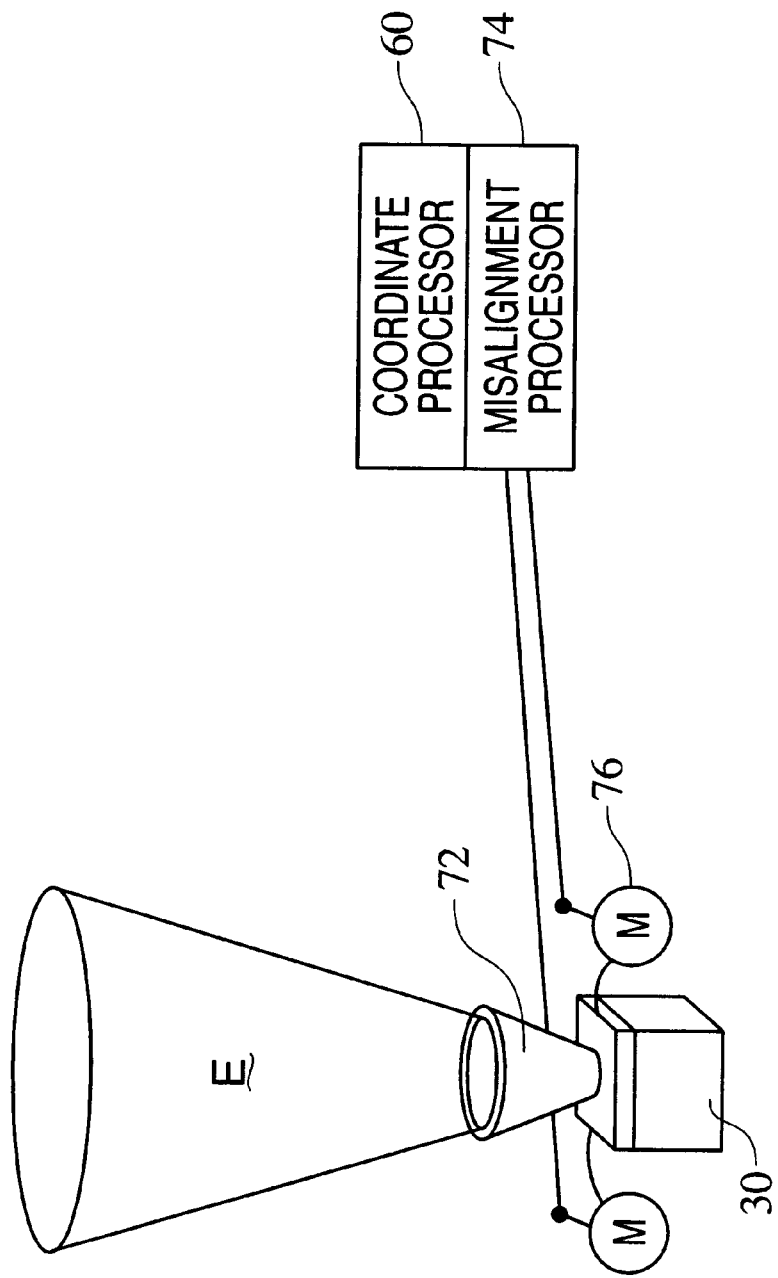
FIG. 4 is a diagrammatic illustration of collimator adjustment to correct for induced errors.

Referring to FIG. 4, the x-ray source 30 includes a collimator 72 which predicts the x-ray beam through the examination region E onto the x-ray detector 28 with little or no overscan. When the detector and source deflect by different amounts, the source and detector may become misaligned. To correct the misalignment, a misalignment processor 74 calculates a misalignment correction and controls a servomotor 76 to reposition the collimator 72 thus realigning the x-ray beam onto the detector.

The use of three-axis accelerometers on the position sensitive imaging components can result in an overall reduction in system cost. Less massive structures can be used because precise positional information is readily available even when the structures deflect. The invention thus has the advantage that a highly versatile positioning structure, such as a fluoroscopic C-arm or other devices that are subject to mechanical distortion, can be used for a high precision image procedures, such as volume image reconstructions. Moreover, accelerometer use can also result in increased system availability. Time consuming calibration and re-calibration runs to correct for wear and aging are no longer required since position correcting data is developed on-the-fly during the diagnostic imaging procedure.

Figure 5:
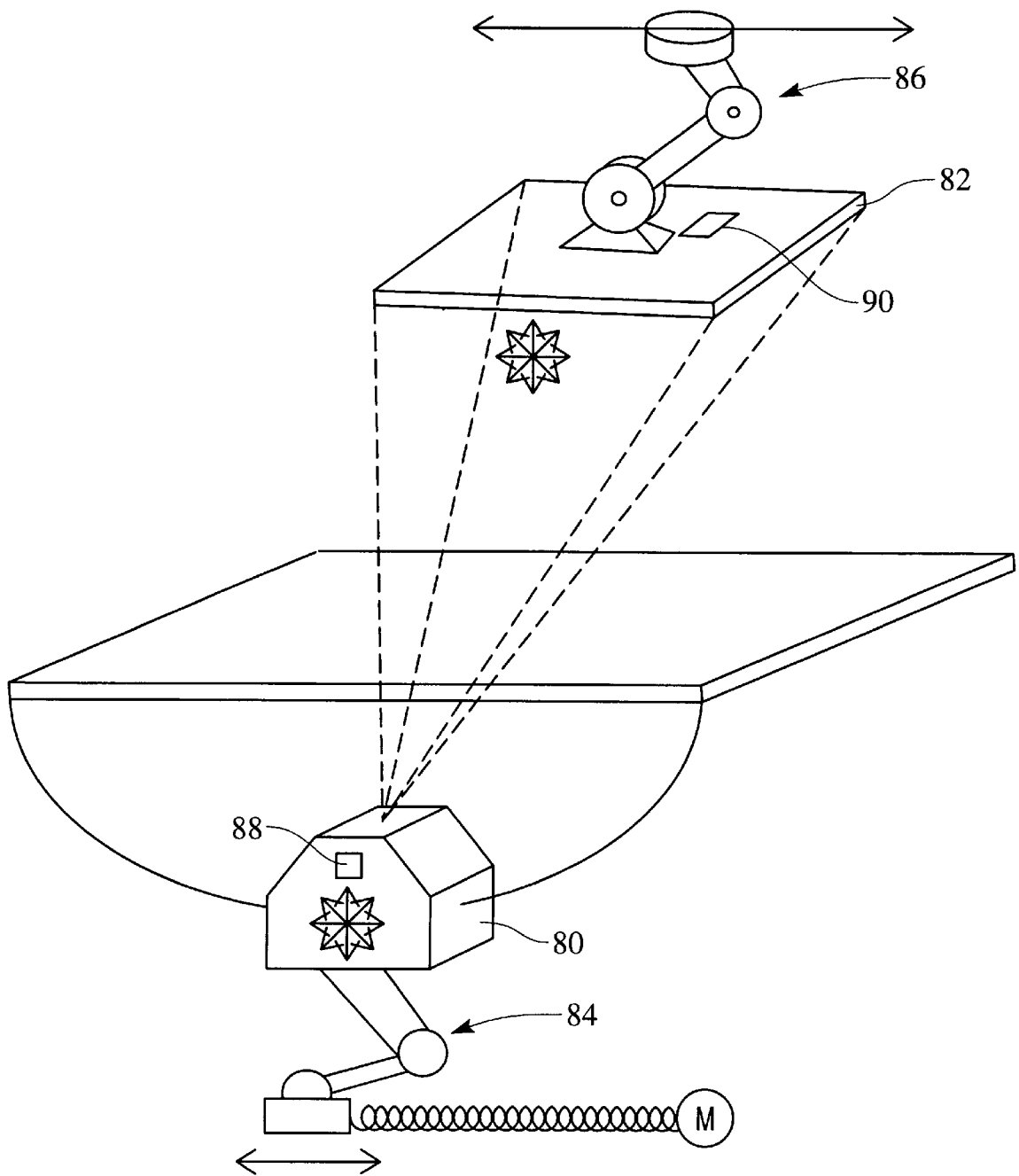
FIG. 5 shows a diagrammatic illustration of an alternate embodiment of the present invention.

Now referring to FIG. 5, an independent movable radiation source 80 and radiation detector array 82 can be utilized. In other words, the source and the detector are not connected to a common frame. In a preferred embodiment, the source 80 is mounted to the floor by a mechanical support structure 84 capable of inducing motion. The detector is attached to a similar three degrees of movement structure 86 suspended from the ceiling. MEMS accelerometers 88, 90, as discussed above with reference to FIG. 1, are mounted to the source and the detector. Preferably a fixed repeatable docking position is defined as a reference position for zeroing the accelerometers.

The invention has been described with reference to the preferred embodiments. Potential modifications and alterations will occur to others upon a reading and understanding of the specification. For example, accelerometers could also be employed in other medical imaging applications such as fluoroscopy, angiography, ultrasound, etc. It is our intention to include all such modifications and alterations insofar as they come within the scope of the appended claims, or the equivalents thereof.

Having thus described the preferred embodiment, the invention is now claimed to be:

1. A diagnostic imaging apparatus comprising:
   an x-ray source for transmitting a beam of x-rays through an examination region;
   a detector positioned to receive the beam and generate electric signals indicative of an intensity of the received beam; and
   a first accelerometer associated with the x-ray source such that a change in acceleration of the source corresponds to a change in acceleration of the accelerometer, the first accelerometer generating a first acceleration signal indicative of acceleration along at least one dimension.

2. The diagnostic imaging apparatus of claim 1 further comprising:
   a second accelerometer for measuring acceleration of the detector in at least one dimension and generating a second acceleration signal indicative of the measured acceleration.

3. The diagnostic imaging apparatus of claim 2 further comprising:
   a position calculator for mathematically calculating (1) a position of the source from data including the first acceleration signal, and (2) a position of the detector from data including the second acceleration signal.

4. The diagnostic imaging apparatus of claim 3 further comprising:
   a means for producing relative motion between the source and the examination area.

5. The diagnostic imaging apparatus of claim 4, wherein the means for producing relative motion moves the source to a plurality of predetermined positions, the apparatus further comprising:
   an image reconstruction processor for receiving (1) a plurality of image data views from the detector at the predetermined positions, (2) and the positions of the source and the detector calculated by the position calculator; and for processing the image data views into a three-dimensional image representation.

6. The diagnostic imaging apparatus of claim 5 wherein the x-ray source generates a cone-beam and the detector includes a planar array of solid state detectors.

7. The diagnostic imaging apparatus of claim 6 where the x-ray source and detector are mounted at opposing ends of a C-arm.

8. The diagnostic imaging apparatus of claim 6 wherein the x-ray source and the detector are mounted to independently movable supports.

9. The diagnostic imaging apparatus of claim 6 further comprising:
   a collimator movably mounted adjacent to the x-ray source for focusing the cone beam onto the detector; and
   a misalignment processor for receiving the position of the source and the detector, and for controlling a drive system mechanically linked to the collimator, the collimator being moved by the drive system to focus the cone beam onto the detector.

10. A radiographic imaging apparatus including a penetrating radiation source which generates a cone beam of radiation and a radiation detector which receives the cone beam of radiation and is sampled to generate corresponding views of image data, a mechanical structure for supporting the radiation source and the detector on opposite sides of an examination region, a drive for moving the mechanical structure to move the radiation source and the detector around the examination region, and a reconstruction processor for reconstructing a plurality of the image data views into a volumetric image representation, further comprising:

a first accelerometer for measuring acceleration of the radiation source and generating a first acceleration signal indicative of the measured acceleration;

a second accelerometer for measuring acceleration of the detector and generating a second acceleration signal indicative of the measured acceleration; and a position processor which integrates the first and second acceleration signals and determines a position of the radiation source and a position of the detector corresponding to each sampling of the detector to generate one of the image data views, the position processor being connected with the reconstruction processor for conveying the determined radiation source and detector positions to the reconstruction processor.

11. The radiographic imaging apparatus of claim 10 wherein the mechanical support includes:

a C-arm, the radiation source being mounted at one end of the C-arm and the detector being mounted to an opposite end, a central position of the C-arm being connected to the drive for rotation about a horizontal axis.

12. The radiographic imaging apparatus of claim 10 wherein the accelerometers include 3-axis MEMS accelerometers.

13. The radiographic imaging apparatus of claim 10 further comprising:

a collimator mounted to the radiation source for focusing the cone beam of radiation on the detector;

a misalignment processor which receives the radiation source and detector position signals and determines misalignment therebetween; and a servo-drive for repositioning the collimator to maintain the cone beam focused on the detector.

14. A radiographic apparatus including:

a radiation source mounted at a first position for transmitting a beam through an examination region;

a detector mounted at a second position for receiving the beam and generating signals indicative of intensity of the beam; and a first accelerometer mounted for detecting a first acceleration of the radiation source relative to at least one dimension as the radiation source is moved.

15. The radiographic apparatus of claim 14 further including:

a second accelerometer mounted for detecting a second acceleration of the detector relative to at least one dimension as the detector is moved.

16. The radiographic apparatus of claim 15 further including:

a converter for mathematically calculating:

a calculated position of the source from data including the detected first acceleration, and a calculated position of the detector from data including the second acceleration; and an image reconstruction processor for generating an image representation from a plurality of the detector signals and the calculated positions of the source and the detector.

17. A process for diagnostic imaging comprising:

transmitting a beam of x-rays from an x-ray source through an examination region to a radiation detector;

moving at least the x-ray source from a starting position relative to the examination region;

at each of a plurality of positions, sampling the detector to generate a view of image data indicative of an intensity measured by the detector;

monitoring acceleration of the x-ray source as it moves relative to the examination region;

corresponding to each sampling of the detector, determining a position of the radiation source relative to the starting position based on information including the monitored acceleration; and reconstructing the views of image data into a volumetric image representation in accordance with the determined positions of the x-ray source.

18. The process of claim 17 further comprising:

moving the detector from the starting position relative to the examination region;

monitoring acceleration of the detector as it moves relative to the examination region;

corresponding to each sampling of the detector, determining a position of the detector relative to the starting position based on information including the monitored acceleration; and in the reconstruction step, reconstructing the views in accordance with the determined source position and the determined detector position.

19. The process of claim 17 wherein the steps of determining the positions of the radiation source and the detector includes integrating the monitored accelerations to determine spatial displacement relative to the starting positions.

20. The process of claim 18 further comprising:

from the determined positions of the radiation source and the detector, determining misalignment of the x-ray beam and the detector; and in response to any determined misalignment, redirecting the beam.

21. The process of claim 18 wherein monitoring acceleration of the radiation source includes:

monitoring acceleration along 3 coordinates; and monitoring acceleration of the detector includes monitoring acceleration along 3 coordinates.

* * * * *